United States Patent [19]
Nikolaychik et al.

[11] Patent Number: 5,702,715
[45] Date of Patent: Dec. 30, 1997

[54] REINFORCED BIOLOGICAL SEALANTS

[75] Inventors: Victor V. Nikolaychik, Mequon; Brent A. Burdick, Brookfield; Leonid V. Nikolaychik, Bayside, all of Wis.

[73] Assignee: Drying Technology, Bayside, Wis.

[21] Appl. No.: 549,365

[22] Filed: Oct. 27, 1995

[51] Int. Cl.$^6$ .................................................. A01N 25/34
[52] U.S. Cl. ........................ 424/402; 106/124.5; 424/445; 424/404; 514/2
[58] Field of Search .................... 424/402, 404, 424/445; 514/2; 106/124.5

[56] References Cited

U.S. PATENT DOCUMENTS

| | | | |
|---|---|---|---|
| 4,359,049 | 11/1982 | Redl et al. | 128/218 PA |
| 4,427,651 | 1/1984 | Stroetmann | 424/46 |
| 4,627,879 | 12/1986 | Rose et al. | 106/124 |
| 4,874,368 | 10/1989 | Miller et al. | 604/82 |
| 5,185,001 | 2/1993 | Galanakis | 604/5 |
| 5,226,877 | 7/1993 | Epstein | 604/35 |
| 5,330,974 | 7/1994 | Pines et al. | 514/21 |
| 5,407,671 | 4/1995 | Heimburger et al. | 424/94.1 |
| 5,506,127 | 4/1996 | Proba et al. | 435/214 |

FOREIGN PATENT DOCUMENTS

| | | |
|---|---|---|
| 1168219 A | 5/1983 | U.S.S.R. |

OTHER PUBLICATIONS

Adamyan et al., Use of fibrin glue in obstetrics and gynecology: A review of the literature. *Int. J. Fert.* 36:76–7, 81–88 (1991). (Abstract only).

Auger et al., Role and innocuity of Tisseel, a tissue glue, in the grafting process and in vivo evolution of human cultured epidermis. *Brit. J. Plast. Surg.* 46: 136–142 (1993).

Brown et al., Increased wound contraction with fibrin glue-treated skin grafts. *Arch. Surg.* 127:404–406 (1992). (Abstract Only).

Dean et al., Benefits of adjuvant fibrin glue in skin grafting. *Med. J. Austral.* 160:526–527 (1994).

Fasol et al., Experimental use of a modified fibrin glue to induce site–directed angiogenesis from the aorta to the heart. *J. Thoracic Cardiovasc. Surg.* 107: 1432–1439 (1994).

Fibrin Sealant: Characteristics and Clinical Uses. Abstracts, pp. 2, 14–16, 20, 30–31, 33–41, 45–46, 67. (1994).

Flahiff et al., Mechanical properties of fibrin adhesives for blood vessel anastomosis. *J. Biomed. Mat. Res.* 26: 481–91 (1992). (Abstract only).

Fontana et al., Cartilage chips synthesized with fibrin glue in rhinoplasty. *Aesth. Plast. Surg.* 15: 237–240 (1991).

Gauwerky et al., The effect of fibrin glue and peritoneal grafts in the prevention of intraperitoneal adhesions. *Arch. Gynecol. Obstret.* 247:161–166 (1990).

Gibble and Ness, Fibrin glue: The perfect operative sealant? *Transfusion* 30:741–747 (1990).

Glimåker et al., Avoiding blow–out of the aortic stump by reinforcement with fibrin glue. A report of two cases, *Eur. J. Vasc. Surg.* 7:346–348 (1993).

Goudarzi et al., Organerhaltung oder partielle resektion der traumatischen milzrupturen im kindesalter unter anwendung von fibrinkleber; eine alternative zur splenektomie und lienalen autotransplantation. *Chirurgische Gastroenterologie* 9(Suppl 2): 132–135 (1993).

(List continued on next page.)

*Primary Examiner*—Thurman K. Page
*Assistant Examiner*—Kathryne E. Shelborne
*Attorney, Agent, or Firm*—Quarles & Brady

[57] ABSTRACT

A reinforced biological sealant is disclosed. The sealant includes a fibrinogen composition adapted to be applied to a wound, and a solid thrombin composition layered on the fibrinogen film. At least one of the fibrinogen or thrombin compositions comprises a reinforcement filler. Means are provided for activating formation of a fibrin mesh from the fibrinogen and thrombin compositions, thereby effecting hermetization and hemostasis of the wound.

15 Claims, 3 Drawing Sheets

OTHER PUBLICATIONS

Hamm et al., Experimental studies in animals on the use of a fibrin glue from the human plasma fraction Cohn I in nerve reconstruction. *Folia Haematol.* 115: 208–212 (1988). (p. 208 only).

Heidenreich, W., Verbesserung der mesh-graft-methode durch einsatz eines fibrinklebers. Zent.bl. Gynakol. 113: 731–734 (1991).

Hombrouckx et al., Fibrin sheet covering subclavian or femoral dialysis catheters. *Artificial Organs* 18: 322–324 (1994).

Isogai et al., Use of fibrin glue to minimize bleeding of microvascular repairs in hypertensive rats. *Microsurgery* 13: 321–4 (1992). (Abstract only).

Kram et al., Use of concentrated fibrinogen in experimental tracheal repair. *J. Biomed. Mat. Res.* 20: 579–687 (1986). (p. 579 only).

Marchac and Sandor, Face lifts and sprayed fibrin glue: An outcome analysis of 200 patients. *Brit. J. Plast. Surg.* 47: 306–309 (1994).

More and Harvey, Purification technologies for human plasma albumin. pp. 261–306 in *Blood Separation and Plasma Fractionation*, J. R. Harris (ed.), New York: Wiley-Liss. 1991. (pp. 261–263 only).

Mosesson, M.W., The roles of fibrinogen and fibrin in hemostasis and thrombosis. *Seminars in Hematology*, 29: 177–188 (1992).

Nicholas and Dulchavsky, Successful use of autologous fibrin gel in traumatic bronchopleural fistula: case report. *J. Trauma* 32: 87–88 (1992). (Abstract only).

Ono et al., Apatite-wollastonite containing glass ceramic granule–fibrin mixture as a bone graft filler: Use with low granular density. *J. Biomed. Mat. Res.* 24: 11–20 (1990).

Rossi et al., Une alternative simple dans le traitement des fistules urinaires: La colle de fibrine. *Progres en Urologie* 1: 445–448 (1991). (Abstract only).

Saltz et al., Experimental and clinical applications of fibrin glue. *J. Plast. Reconst. Surg.* 88: 1005–1015 (1991).

Seguin et al., Fibrin sealant improves surgical results of type A acute aortic dissections. *Annals of Thoracic Surg.* 52: 745–748 (1991). (Abstact only).

Seguin et al., Aortic valve repair with fibrin glue for type A acute aortic dissection. *Annals Thoracic Surg.* 58: 304–307 (1994).

Sigma catalog. Biological buffers, pp. 1685–1688. Biological detergents, pp. 1537–1544.

Silbertsein et al., An autologous fibrinogen–based adhesive for use in otologic surgery. *Transfusion* 28: 319–321 (1988). (p. 319 only).

Silverstein et al., Fibrin glue anastomosis compared to conventional sutured vasovasostomy in the rat. *J. Urology* 145: 1288–1291 (1991). (Abstract only).

Spernol et al., Morphology of rabbit oviduct after reanostomosis with fibrin glue. *Int. J. Gynaecol. Obstet.* 22: 295–301 (1984).

Steube et al., Fibrin glue on the Cohn I fraction basis in repairing cerebral and dura defects—An experimental study on rats. *Folia Haematol.* 115: 213–217 (1988). (p. 213 only).

Surgical and Surgical Nu–Knit Product Information. pp. 1094–1095.

Tawes et al., Autologous fibrin glue: The last step in operative hemostasis. *Am. J. Surgery* 168: 120–122 (1994).

Van Velthoven et al., Fibrin tissue adhesive sealant for the prevention of CSF leakage following transsphenoidal microsurgery. *Acta Neurochir (Wien)* 109: 26–29 (1991). (pp. 26, 28 only).

Vietri et al., L'impiego della cotta di fibrina umana nella patologia fistolosa del polmone. *Giornale di Chirurgia* 12: 399–402 (1991). (English abstract only).

REINFORCED BIOLOGICAL SEALANTS

FIELD OF THE INVENTION

The present invention relates generally to reinforced biological sealants, which provide hermetization, hemostasis, and topical delivery of medications to wounds, including surgically open surfaces or sutures.

BACKGROUND OF THE INVENTION

In wound healing, the final stage of the coagulation cascade results in the formation of insoluble fibrin from fibrinogen in the presence of other plasma components, most notably, thrombin and factor XIII; thrombin converts fibrinogen and factor XIII into their reactive forms. The fibrin thus formed is deposited on the wound, where the fibrin stops bleeding both chemically and mechanically.

Together with improvements in modern surgical suturing techniques and intraoperative hemostasis, wound treatment has been greatly advanced by the use of suitable supplementary materials, such as tissue glues or adhesives, to accelerate hemostasis as well as to optimize conditions and control of wound closure. Fibrin-based biological glues have proven particularly advantageous over non-biological adhesives because fibrin-based glues mimic the natural coagulation cascade and enhance the healing process. Fibrin glues provide excellent hemostatic and sealing properties. In addition, such glues are non-toxic.

Typically, fibrin adhesive is prepared by applying the components in liquid form on the desired tissue, either by sequential addition of the individual liquid components, or by pre-mixing the components to allow polymerization to commence. For example, when the components are applied to the tissue in sequence, fibrinogen solution is first applied onto the tissue. Next, small amounts of a highly concentrated thrombin and/or factor XIII solution are dropped onto the tissue-supported fibrinogen solution for coagulation. Usually, a fibrinolysis inhibitor is added in order to prevent a premature lysis and thus the premature dehiscence of the adapted tissue parts. However, this technique is expensive and complicated because of the necessary separate preparation, storage and application of the individual components making up the adhesive. Additionally, the technique is time-consuming and difficult to control.

In another method of preparing fibrin adhesive, the components are mixed together before application to the tissue. Deep-frozen fibrinogen solution is thawed and thrombin and calcium chloride are added; the mixture is held for a period of time until polymerization becomes noticeable by an increase in viscosity of the mixture. The reaction mixture is then applied onto the tissue parts to be joined. In many cases, the expenditure for preparing the "fibrin adhesive" suitable for use and the short life of the preparation (not more than 12 hours) ready for use have proven to be an impediment, and the application is difficult for the practicing physician because he or she cannot reliably determine the short-time interval of a still liquid adhesive suitable for use. Additionally, it is hard to apply this solution to complex geometry bodies, like blood vessels.

Various types of fibrin glues are disclosed in the prior art. For example, U.S. Pat. No. 4,427,651 to Stoetmann discloses a sprayable preparation for accelerated hemostasis and optimized biochemical control of wound closure. The Stoetmann preparation contains a powdery mixture of 15 to 60% by weight of a dessiccating and stabilizing agent, albumin, globulin and/or fibrinogen. The powdery mixture is suspended in a low-boiling anhydrous solvent which is used as a propellant. For effective wound closure and coverage, a spray jet of this suspension is directed onto the wound under evaporation of solvent so that substantially only the dry, solid powdery mixture reaches the wound.

U.S. Pat. No. 5,185,001 discloses a method of preparing autologous plasma fibrin perioperatively to induce local hemostasis. The autologous plasma fibrin is thereafter simultaneously expelled onto a treatment site along with a physiologically acceptable thrombin solution to effect hemostasis at the site. The autologous plasma fibrin and thrombin solutions are also disclosed.

U.S. Pat. No. 5,407,671 to Heimburger, et al. discloses a one-component tissue adhesive containing, in aqueous solution, fibrinogen, factor VIII, a thrombin inhibitor, prothrombin factors, calcium ions, and other components where appropriate. The Heimburger adhesive can be freeze-dried and stored until use. When the adhesive is needed, it is reconstituted to a liquid form from the freeze-dried solid by dissolving the solid in a solvent such as water.

Typically, application of fibrin glue is carried out with a double-barreled syringe apparatus which allows for simultaneous application through a blunt-tipped needle of equal amounts of the fibrinogen and thrombin solutions to form a gel on the patient's tissue, to seal the wounded or suture site against further release of blood, or dislocation of tubular formation, graft skin, and hard tissue, or liquorrhoea, or pneumothorax. Examples of means to apply fibrin glue include U.S. Pat. No. 4,359,049 to Redl, et al., which discloses a syringe-type apparatus for applying a tissue adhesive, and U.S. Pat. No. 4,874,368 to Miller, et al., which relates to a fibrin glue delivery system comprising a pair of syringe tubes that can be actuated by plungers simultaneously or independently.

Alternately, materials comprising fibrin glue can be applied by spray application of the liquid components with forced sterile gas, by mixing equal proportions of the solutions on application. Spray application is advantageous because it is possible to coat extensive tissue surfaces with a small amount of fibrin and thrombin, and spray application systems are readily available. The disadvantages include low mechanical strength of the resulting glue and inhomogeneous distribution of the glue on tubular tissue. Furthermore, because the optimal distance for spray application is about 10 to 15 cm from the tissue surface, spray application is virtually impossible to use in small areas such as those typical in otology and neurology.

Although fibrin based glues are being used in many areas of surgery with increasing success, there is a limit to the effectiveness of fibrin glues because all such glues are applied as liquids. Generally, liquid-applied glues have low mechanical characteristics. In addition, formulation of such glues is time consuming, and solubilization of thrombin and, more important, fibrinogen, is difficult. Furthermore, the two-component fibrin glue mixture of thrombin and fibrinogen is slow to solidify, and offers only low pressure resistance. Also, it is difficult to form solid rings around tubal structures like blood vessels or Fallopian tubes by using liquid components.

Examples of the problems of liquid-applied fibrin glues abound. Thus, when fibrin adhesives were used for connection of tubal stumps in glued anastomoses, intraluminal fibrin deposits resulted and some deposits were detected three months after application of the adhesive. These deposits can close down the tubal opening. In addition, when the stumps have lumina of different widths and a lumen approximating technique is necessary, accurate layer for layer matching cannot be achieved with liquid-applied fibrin glues. Also, thrombosis secondary to the inadvertent intravascular penetration of the liquid component of fibrin glue theoretically is possible. Although liquid-applied fibrin adhesives provide a good outcome of anastomotic sites in colonic and small bowel surgery, on the other hand, such adhesives promote postoperational peritoneal adhesions, one of the major problems of intraabdominal surgery.

SUMMARY OF THE INVENTION

In one embodiment, the present invention is a prefabricated, reinforced biological sealant. The sealant comprises a fibrinogen composition and a thrombin composition layered on the fibrinogen composition. At least one of the fibrinogen or thrombin compositions comprises a reinforcement filler. The prefabricated biological sealant will be placed in position and activated with an aqueous solution.

In one preferable form of the present invention, both the fibrinogen and thrombin composition are films. In another embodiment of the present invention, the thrombin composition is a solution.

In another embodiment, the present invention is an activated reinforced biological sealant. The sealant includes a solid fibrinogen film adapted to be applied to a wound, and a solid thrombin film layered on the fibrinogen film. At least one of the fibrinogen or thrombin compositions is reinforced. Means are provided for activating formation of fibrin from the fibrinogen and thrombin films so as to form a fibrin mesh, thereby effecting hermetization and hemostasis of the wound.

Another embodiment of the present invention discloses a method for treating a wound. Preferably, a reinforced fibrinogen film is applied to the wound and a reinforced thrombin film is layered on the reinforced fibrinogen film. The films are then activated so as to form a fibrin mesh over the wound, thereby effecting hermetization and hemostasis of the wound.

In another embodiment, medications, such as antimicrobials or stimulators/inhibitors, are included in the reinforced fibrinogen film to effect topical delivery of the medication to the wound.

It is an object of the present invention to provide a reinforced biological sealant useful in providing hermetization and hemostasis to wounds, including surgically open surfaces and sutures.

It is another object of the present invention to provide a reinforced biological sealant useful in providing topical delivery of medications to wounds, including surgically open surfaces and sutures.

It is another object of the present invention to provide close apposition of healing structures and a reduction in the number of sutures required.

Other objects, advantages and features of the present invention will become apparent after review of the specification, claims and drawings.

BRIEF DESCRIPTION OF THE DRAWINGS

FIG. 1A illustrates a planar thrombin or fibrin film. FIG. 1F is a structure adapted to fit a half-cylindrical with side attachments. FIG. 1G is adapted to fit a cylindrical shape with a top flange. FIG. 1H is adapted to fit a cylindrical shape. FIG. 1I is adapted to fit a cylindrical shape with top flange.

DETAILED DESCRIPTION OF THE INVENTION

The present invention is a reinforced biological sealant (also referred to as "RBS" in the following discussion) for use in treating wounds, including surgically open surfaces or sutures. In one embodiment, the present invention is a reinforced prefabricated sealant comprising a fibrinogen composition adapted to be applied to a treatment condition and a thrombin composition layered onto the fibrinogen composition. Either the fibrinogen or thrombin composition is reinforced. Preferably, both compositions are reinforced.

By "prefabricated" we mean that the biological sealant is prepared externally to the treatment site and is adapted to be stored or transported as needed. By "composition" we mean either a solid or liquid composition. Preferably, the compositions are solid. Most preferably, the compositions are films.

Figure 1A:
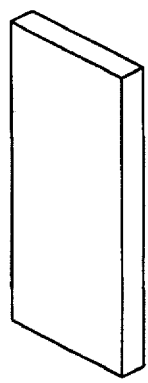
FIGS. 1A, B and C illustrate planar films.
Figure 1B:
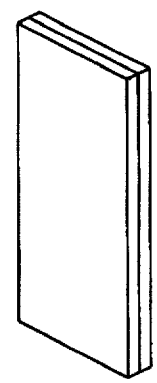
FIGS. 1B and C illustrate layered reinforced films.
Figure 1C:
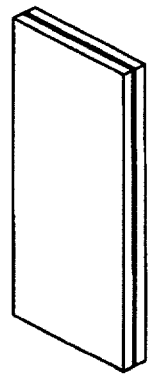
FIG. 1 illustrates alternative shapes of the reinforced biological sealant of the present invention.
FIG. 1D illustrates interlocking between fibrinogen/thrombin films.
FIG. 1E illustrates a ring structure, suitable for application as an interphase.
FIGS. 1F through J illustrate the reinforced films of the present invention adapted to contact cylindrical structures, such as blood vessels.
Figure 1D:
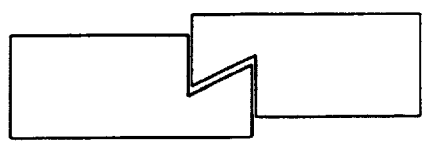
Figure 2:
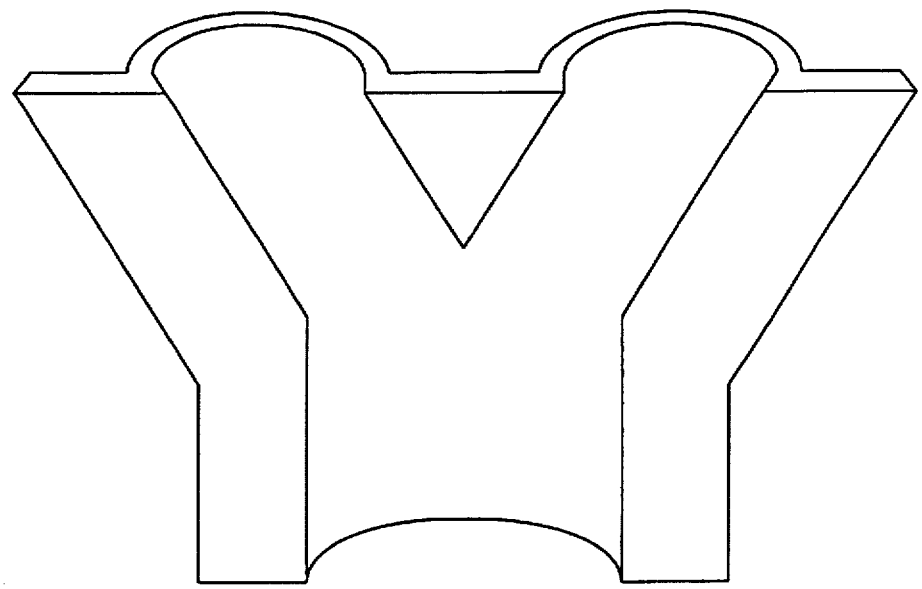
FIG. 2 illustrates another alternative shape of the reinforced biological sealant of the present invention adapted to fit a half-cylindrical structure that branches off into two half-cylinders.
Figure 1E:
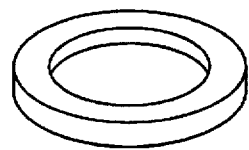
Figure 1F:
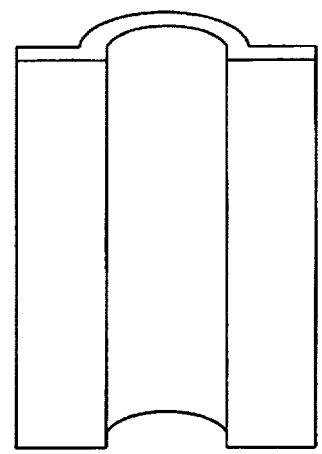
Figure 1G:
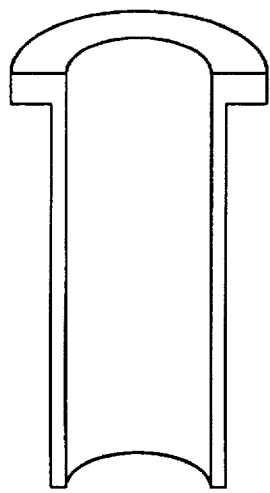
Figure 1H:
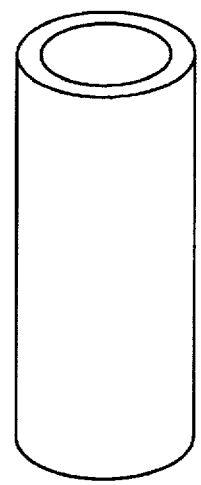
Figure 1I:
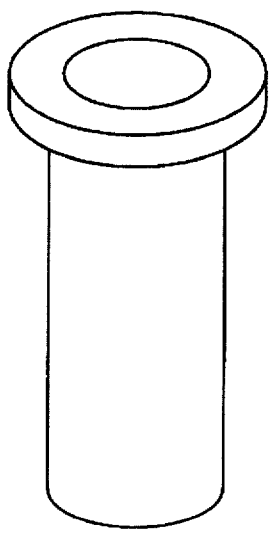

Preferably, reinforced biological sealants of the present invention include substantially flat, layered, solid reinforced fibrinogen and thrombin films layered over a wound. As is illustrated in FIGS. 1–2, the RBS of the present invention can also be prepared in various shapes, such as half cylinders, cylinders, rings or a combination thereof, to fit a particular sealant demand.

When the fibrinogen and thrombin films are layered over a wound, a solvent such as water, blood, plasma, Ringer solution and other saline solutions may be applied to the layered films, thereby activating the formation of fibrin from the fibrinogen and thrombin. This stage is often described as "gelling". The fibrin forms a meshwork over the wound, mimicking the last stage of the clotting cascade necessary for wound healing. Formation of the fibrin meshwork is regulated by the concentration of fibrinogen, calcium ions, and thrombin activity. One may monitor the formation of the fibrin meshwork visually because the translucent fibrinogen and thrombin compositions will become opaque.

Reinforcement fillers suitable for use in the present invention provide mechanical reinforcement. These materials preferably are a glass when a film is formed and are preferably materials that have already been allowed in medical applications. The material is useful as a bulking agent or vehicle and is soluble in aqueous solutions. Preferably reinforcement fillers include polyethyleneglycol, myo-inositol, polyvinylpyrrolidone, bovine serum albumin (1–20 g/liter, preferably 10 g/liter), FICOLL, dextran, mannitol, sodium chlorate (9–40 g/liter, preferably 27 g/liter) or a combination thereof. It is not necessary that the reinforcement filler be the same material in the fibrinogen or thrombin layer.

If one wish to evaluate whether a particular material was suitable as a reinforcement filler, one could replicate the experiments described below using the candidate filler. The candidate reinforcement filler would then be compared to the reinforcement fillers described below. Note that Table 8 describes the breaking strength of a sample RBS. At 2 minutes, the critical pressure of the sample RBS was 320 mm Hg while the critical pressure of prior art fibrin adhesive was only 40 mm Hg. A suitable reinforcement filler will provide a critical pressure of at least 150 mm Hg, preferably 200 mm Hg, under the same conditions.

In general, to make the reinforced fibrinogen and thrombin compositions, aqueous fibrinogen and thrombin solutions are prepared as described below. Preferably, a uniform, precisely measured volume of each respective solution is then dispensed onto a non-stick, preferably hydrophobic, polymer support surface. The polymer-supported composition is then typically dried to a residual water content of less than about 8%, preferably less than about 4%. Drying is carried out according to standard procedures known in the art.

Typically, compositions are dried for about 5 to 24 hours at temperatures in the range of about 10° C. to 50° C., at a pressure in the range of about 25 Torr to 300 Torr. The preferred drying condition is about 15° C. for about 6 hours at about 50 Torr.

Preparation of Fibrinogen and Thrombin Films

Commercial active fibrinogen can be acquired from such vendors as Sigma or Miles (Bayer), or can be prepared from plasma by the cryoprecipitation technique well known to those skilled in the art. Alternatively, fibrinogen prepared by recombinant methods is suitable for use.

Commercial active thrombin can be acquired from Sigma, St. Louis, Mo. or from Johnson & Johnson as thrombin topical USP, THROMBOGEN.

To make the fibrinogen and thrombin solutions used to prepare the films, the necessary chemicals are measured, weighed, and dissolved in about 800 ml of deionized or distilled water. Tables 1 and 2 disclose preferable solution compositions used to prepare the fibrinogen and thrombin films, respectively.

TABLE 1

Fibrinogen Solution Composition.

| Component | Composition Range g/liter | Composition Preferred g/liter |
|---|---|---|
| Fibrinogen | 5-70 | 35.0 |
| Glycerol | 100-200 | 150.0 |
| TRIS | 6.25-24.2 | 12.1 |
| Caprylic Acid | 10-40 | 12.0 |
| Triton X-100 | 0.5-1.5 | 1.0 |
| Reinforcement Filler | 50-700 | 500.0 |

The glycerol in Tables 1 and 2 is used as a plastificator. Other plastificators would also be suitable in the present invention. TRIS is used as a pH adjustment. Other suitable alternatives for TRIS are other Good buffers such as hepes, pipes, and tricine and other buffers with a pKa of between 6.8 and 8.3. Triton X-100 is a non-ionic detergent and stabilizer and may be substituted by other detergents and stabilizers. Caprylic acid may be substituted by other protective agents against denaturation such as alginic acid.

It is preferable to completely dissolve each chemical before adding the next chemical. The aqueous fibrinogen and thrombin solutions must be homogeneous and all constituents must be fully dissolved or in suspension. If necessary, after the last chemical is dissolved, the pH is adjusted to 7.0–7.4 and the solution volume is adjusted to 1.0 liter with apyrogenic water. The solution is then degassed.

The solution is dispensed by pump onto a non-stick, preferably hydrophobic, polymer surface to form a film approximately 2 mm thick. The film is then dried until its residual moisture is less than about 8%, preferably less than 4%, of the total wet weight. Both the fibrinogen and the thrombin film may be freeze-dried and stored until needed.

TABLE 2

Thrombin composition.

| Component | Composition Range g/liter | Composition Preferred g/liter |
|---|---|---|
| Thrombin | 1,000-500,000 units | 200,000 units |
| Albumin | 0.1-20 | 5.0 |
| TRIS | 6.25-24.2 | 12.1 |
| Alginic Acid | 10-40 | 20.0 |
| Factor XIII | 1,000-10,000 units | 5,000 units |
| CaCl$_2$ | 1-145 mg/liter | 100.0 mg/liter |
| Reinforcement Filler | 50-700 | 500.0 |

The presence of Factor XIII is preferred but not necessary. Factor XIII makes the mesh-work more stable. In the presence of Factor XIII, covalent crosslinking of the fibrin mesh occurs by formation of glutamil-lysil isopeptide bonds, thereby yielding a well defined organization or network.

Fibrinogen is the most critical reagent in RBS because fibrinogen controls the material properties of the RBS, such as gel rigidity, fiber thickness, fiber mass density, pore size, and fiber branch point density. These features determine the rigidity and strength of the sealant, how easily other molecules can diffuse within the gel, and how long the RBS may survive.

As is illustrated in Table 3, thrombin content affects the rapidity of fibrin meshwork formation and plays a major role when the hemostatic and sealing properties of the composition are the most important clinical consideration. For example, meshwork formation in less than 10 seconds can be induced by a thrombin concentration of 500,000 units/liter (1 NIH unit of thrombin activity is capable of catalyzing 1 g of fibrinogen in 15 seconds). Conversely, meshwork formation can be slowed from 1 to 3 minutes by using thrombin concentrations of about 1,000 units/liter. Increased thrombin levels actually lower the tensile strength of meshwork.

TABLE 3

| Fibrinogen Adhesive, g/liter | Thrombin, units/liter | Polymerization Time, sec. | |
|---|---|---|---|
| | | RBS | Fibrin |
| 5 | 1,000 | 120 | 118 |
| 20 | 1,000 | 116 | 117 |
| 60 | 1,000 | 117 | 118 |
| 5 | 20,000 | 28 | 29 |
| 20 | 20,000 | 29 | 28 |
| 60 | 20,000 | 27 | 26 |
| 5 | 500,000 | 10 | 11 |
| 20 | 500,000 | 9 | 8 |
| 60 | 500,000 | 8 | 8 |

In one embodiment of the present invention, one would add a solid material such as ceramic materials (in a concentration in the composition from about 2% to 50%), calcium phosphate, aluminum phosphate, aluminum oxide, or glass ceramics, to be used as bone and teeth substitutes or for hard tissue replacement. These solid materials would be added in addition to the reinforcement filler described above. From a chemical point of view, such solid fillers are analogous to the mineral part of calcified tissues and mimic the structure of natural bone, thus allowing natural bone growth.

In addition to the fibrinogen and thrombin reagents in the respective solutions, it is preferable to include a surfactant at a concentration sufficient to inhibit bubble formation during solution preparation, and to stabilize the protein native state during drying process and storage. Examples of such stabilizers-surfactants include sodium octanate(caprylate) (10–40 g/liter, preferably about 27 g/liter) and/or sodium N-acetyl tryptophanate (8–45 g/liter, preferably about 30 g/liter), which are approved for medical use.

The reinforced biological sealants of the present invention may also include one or more medications, such as antiseptic and anti-inflammation agents, at concentrations sufficient to prevent development of local infection at the wound site. Suitable antibiotics having a broad or medium spectrum of activity are presented in Table 4.

TABLE 4

| Antibiotic | Range, g/liter | Preferred, g/liter |
|---|---|---|
| Cettazidime | 0.2–5 | 1.0 |
| Cephapirin | 0.1–4.0 | 0.5 |
| Ampicillin | 0.3–6.0 | 3.0 |
| Clindamycin | 0.5–4.0 | 2.0 |
| Vancomycin | 0.2–7.0 | 3.0 |
| Erythromycin | 0.3–8.0 | 5.0 |
| Tetracycline | 1.0–8.0 | 4.0 |
| Tobramycin | 0.2–2.0 | 0.8 |
| Furoxone | 0.1–4.0 | 1.5 |

Nitrofurans such as Furoxone are suitable antimicrobial agents. Furoxone is stable, has a broad antibacterial spectrum and a very low incidence of adverse reactions.

The antibiotics and antiseptics used in a particular film preparation are preferably colored compounds or dyes (or supplemented by such dyes) that can change color under different conditions. For example, Resazurin and Methylene blue may be used as indicators of bacterial contamination. Resazurin is blue and upon bacterial action becomes pink and then colorless. Methylene blue is particularly convenient to use because of its high solubility. Methylene blue can be added to the thrombin solution at a concentration in the range of about 0.2–2.0% w/v (0.25% preferred). Resazurin is also useful in the thrombin solution at a concentration of about 0.05%.

In order to provide control of meshwork formation, the films of the present invention may also include colored indicator substances such as Phenol Red (0.04–0.008%), Thymol Blue (0.04–0.1%), or Furoxone (0.02–0.4%); or antibiotics such as Tetracycline (0.07–0.17%), mithramycin (0.1–0.4%), or chlortetracycline (0.1–0.4%); or colored indicator substances such as Rivanol (0.45–0.75%) or Picric Acid (0.01–0.03%). (All percentages are w/v.) As a result, a color change, such as a green color, will be observed after mixing or penetration of these colored substances (e.g. one is blue, other is yellow), meaning that the gelling reaction of fibrinogen with thrombin is proceeding. Green staining on the wound tissue surface is evidence of the homogeneity of conversion of fibrinogen to fibrin, indicating formation of stable meshwork. Such colored indicators thus provide a double benefit—prevention of infection and evidence of meshwork formation.

As shown in Table 5, the antibiotics and colored substances do not change the rate of meshwork formation or thrombin clotting time at the chosen concentrations.

TABLE 5

| Colored Substance | Concentration, % | Clotting Time, sec. |
|---|---|---|
| Control | — | 18.2 |
| Methylene Blue | 3.0 | 28.0 |
|  | 2.0 | 18.0 |
|  | 0.1 | 18.1 |
| Phenol Red | 0.1 | 24.0 |
|  | 0.08 | 18.3 |
|  | 0.04 | 18.1 |
| Furoxone | 0.4 | 18.0 |
|  | 0.02 | 18.2 |
| Tetracycline | 0.2 | 20.5 |
|  | 0.17 | 18.3 |
|  | 0.07 | 18.1 |
| Rivanol | 0.85 | 91.2 |
|  | 0.8 | 40.3 |
|  | 0.75 | 18.5 |
|  | 0.45 | 18.3 |

EXAMPLES

Example 1

In this in vitro study, the breaking strength and bursting pressure of the RBS of the present invention was compared to the breaking strength and bursting pressure of traditional two-component, liquid-applied fibrin glues. The RBS was prepared from solutions having the compositions set forth in Tables 6 and 7. Thus, the fibrinogen solution was created by mixing together all the components listed in Table 6. The fibrinogen solution was then dispensed by a pump onto a hydrophobic polymer surface to form a uniform liquid film. The liquid film is then dried to a solid fibrinogen film having a residual moisture content of about 4–6%.

Similarly, the thrombin solution was prepared by mixing together all of the components listed in Table 7. The thrombin solution was then dispensed onto a hydrophobic polymer support surface to form a uniform liquid film. The liquid film is then dried to a solid thrombin film having a moisture content of about 4–6%. The RBS was created by layering the resultant solid thrombin film over the solid fibrinogen film. The thrombin-fibrinogen gelling reaction was activated by applying 1 ml of water per 3 $cm^2$ of film to the top of the layered films.

The traditional fibrin glue contained the same concentration and volume of fibrinogen and thrombin as did the fibrinogen and thrombin films of the RBS. The traditional fibrin glue was applied as usual. That is, the fibrinogen and thrombin solutions were drawn up into separate syringes and ejected through needles directly onto the testing surface.

TABLE 6

Fibrinogen composition.

| Component | Concentration, g/liter |
|---|---|
| Fibrinogen | 40.0 |
| Glycerol | 100.0 |
| TRIS | 12.1 |
| Caprylic Acid | 15.0 |
| Dextran 400,000 | 500.0 |
| Tetracycline | 1.0 |

TABLE 7

Thrombin composition.

| Component | Concentration, g/liter |
|---|---|
| Thrombin | 300,000 units/liter |
| Albumin | 5.0 |
| TRIS | 12.1 |
| Triton X-100 | 1.0 |
| Factor XIII | 5,000 units/liter |
| $CaCl_2$ | 100.0 mg |
| Dextran 400,000 | 400.0 |

The breaking strength of the RBS fibrin meshwork and the traditional fibrin glue meshwork was measured with a tensionometer. The results are presented in Table 8.

TABLE 8

Breaking strength of fibrin meshwork.

| | Critical Pressure, mm Hg | |
|---|---|---|
| Time, min. | RBS | Fibrin Adhesive |
| 1 | 280 | 20 |
| 2 | 320 | 40 |
| 5 | 321 | 60 |
| 20 | 316 | 110 |
| 60 | 322 | 206 |
| 180 | 304 | 213 |

In another comparative test, the reinforced biological sealants of the present invention and traditional fibrin glue mixtures were tested for relative bursting pressure. In this test, the fibrinogen content of the RBS and the traditional fibrin glues varied. This test consisted of the topical application of the RBS and the traditional fibrin glues as solidifying rings to a medical grade polyurethane tube having a 4 mm internal diameter. The rings made of the different formulations covered these tubes and repaired 2 mm diameter gaps. Then the rings were subjected to pressurization testing. The results are presented in Table 9.

TABLE 9

Mean bursting pressure after application time 1 minute.

| | Bursting Pressure, mm Hg | |
|---|---|---|
| Fibrinogen, g/l | RBS | Fibrin Adhesive |
| 5 | 280 | 5 |
| 10 | 295 | 8 |
| 50 | 330 | 15 |
| 70 | 336 | 20 |

In 128 samples used for this study, the mean bursting pressure at time 30 seconds was 280 mm Hg in tubes repaired with RBS and from 5 (at low fibrinogen concentration) to 20 mm Hg (at fibrinogen concentration 70 mg per ml) in tubes repaired with different traditional fibrin glues. The difference in bursting pressure between RBS and the traditional fibrin glue formulation was statistically significant at all testing times, although after 60 minutes, when the traditional formulation became stronger, the difference was reduced.

In vitro mechanical testing demonstrated that the reinforced biological sealant of the present invention formulation helps to stabilize the first few minutes following the hermetization and hemostasis. Thus, use of RBS would reduce the incidence of leakage during the first postoperative minutes, providing an opportunity to revascularize ischemic zones (e.g. myocardial infarct).

Example 2

The topical use of RBS to hermetize sutures and prevent bleeding in dogs undergoing surgical suture of anastomoses was evaluated. Tables 10 and 11 present the fibrinogen and thrombin composition used to create the fibrinogen and thrombin films of the RBS. The RBS was made as described in Example 1.

TABLE 10

Fibrinogen composition.

| Description | Concentration, g/liter |
|---|---|
| Fibrinogen | 70 |
| TRIS | 12.1 |
| Triton X-100 | 0.5 |
| Factor XIII | 10,000 units/liter |
| Dextran 70,000 | 400 |
| Tetracycline | 2.0 |

TABLE 11

Thrombin composition.

| Description | Concentration, g/liter |
|---|---|
| Thrombin | 1,000 units/liter |
| Triton X-100 | 1.0 |
| Dextran 70,000 | 300 |
| Methylene Blue | 1 |

A model was developed by bilateral surgical suture of arteria carotis externa in 13 dogs. RBS was applied on the right side, and traditional fibrin glue having the same fibrinogen and thrombin content as the RBS, was applied to the left side of sutured anastomoses, followed by sequential inspection during the operation, and necropsy on postoperative days 1, 3, 5, and 30.

The RBS was more effective after one application in 13 dogs. Hemostasis and hermetization were achieved despite coagulophaty (heparin administration in dose 0.5 mg/kg) and restoration of blood flow at arterial pressure 100/60 mm Hg after 1 minute. There were no re-explorations for bleeding.

In both cases (RBS and traditional fibrin glue) morphological studies revealed good patency of the anastomoses segments without stenosis or occlusions. Thus, the RBS can be used prophylactically to prevent leaks from vessel suture lines and raw surfaces after resections.

Example 3

In order to increase the local antibiotic concentration, an experimental study included topical application of the gentamicin and tetracycline together with fibrin formulations as carriers.

In vivo study, antibiotics were implanted subcutaneously in the neck area of 12 dogs. After 2 days the implanted composition and surrounding tissues were assayed for measurement of tobramycin, gentamicin and tetracycline content. The RBS contained the same composition of fibrinogen and thrombin as described in example 2, while the antibiotics concentration varied. RBS was prepared as two flat dry films (10 mm×10×2 mm size) and then applied to the implanted site. A traditional fibrin adhesive having the same fibrinogen, thrombin, and antibiotic content as the RSB, was similarly applied. The results, presented in Table 12, demonstrate that the RBS was able to maintain antibiotic concentration far better than the traditional fibrin adhesive.

TABLE 12

| Days | Tobramycin content, mg per g implant | |
|---|---|---|
| | RBS | Fibrin Adhesive |
| 3 | 4.108 | 2.731 |
| 6 | 3.224 | 0.574 |
| 9 | 2.003 | 0.107 |
| 12 | 1.139 | 0 |
| 15 | 0.349 | 0 |

Example 4

The replacement of large bone defects is preferentially accomplished with autologous bone grafts. Under many circumstances the graft material may not be available in sufficient quantities nor have an appropriate mechanical quality. Bioceramic granules have been shown to be biocompatible and biodegradable. Such ceramic compounds are able to reproduce bone chemical and structural forms, purity and sterility, ease of handling and placing, minimization of surgical trauma associated with secondary autogenous procedures, control of biodegradation profiles of the synthetic compounds. The initial investigations of bioceramic compounds in humans have included use of bioceramic granules for oral, plastic and orthopaedic surgery procedures.

However, in the body, ceramic material undergoes transformations. The granules are separated from each other, then a dissolution/recrystallization process occurs. As a result, local migration was observed at the surgical placement sites.

To achieve a suitable rate of ossification, firm contact between bioceramic granules and bone tissue is essential. Usefulness of such granules can be enhanced by using them as a mixture with fibrinogen and for thrombin. Benefits in using fibrinogen include: 1) easier handling of the granules and films, 2) assured immobilization of the bioceramic at target site by hardening, 3) hemostatic activity, and 4) promotion of bone formation by accelerating vascularization.

In addition to the above benefits, a fibrinogen-bioceramic composition can contain antibiotics or bacteriostatic substances. In filling bone defects with this composition, healing of the operational wound per primam intentionem is feasible, with retention of the correct anatomical shape, faster ossification and renewal of the mechanical bone strength.

Loss of ovarian function such as occurs at menopause, causes a precipitous loss of trabecular bone. Such bone loss can be prevented by estrogen replacement. Including slow-release derivates of estradiol (1.0–125 mg, preferred 40 mg) in the RBS of the present invention can prevent potential bone destruction. In addition, other growth factors or drugs having osteoconducting potential can be included.

In this study, chemically pure synthetic Macro-Prep ceramic hydroxyapatite granules with particle size 80 micrometers were purchased from Bio-Rad Laboratories (Hercules, Calif. 94547). Fibrinogen was produced from bovine blood by cryoprecipitation technique. Thrombin was purchased from Johnson and Johnson Medical Inc. (Arlington, Tex. 76004-0130).

TABLE 13

| Fibrinogen composition. | |
|---|---|
| Component | Concentration, g/liter |
| Fibrinogen | 50.0 |
| Hydroxyapatite ceramic | 3.0 |
| Sodium citrate | 250.0 |
| Cystatin | 250.0 |
| Aprotinin | 1.0 |
| Triton X-100 | 1.5 |
| Dextran 2,000,000 | 100.0 |

TABLE 14

| Thrombin composition. | |
|---|---|
| Component | Concentration, g/liter |
| Thrombin | 1,000 units/liter |
| Albumin | 3 |
| Dextran 2,000,000 | 200 |

The most important parameter in the healing of bioceramics is the time factor, which is closely related to angiogenesis. Angiogenesis was modelled in culture. Dry films containing mixture of Macro-Prep ceramic hydroxyapatite and an RBS-type fibrinogen solution (See Table 13 for the composition) were placed on the bottom of 35 mm Petri dishes and were treated with an RBS-type solution of thrombin (See Table 14) (1.0 units per ml). After gel formation the surface was washed 5 times with phosphate buffer and 100,000 bovine aorta endothelial cells per dish were inoculated. Cells were suspended in DEEM medium (HyClone Laboratories, Inc., Logan, Utah 84321). As a control, pure Macro-Prep granules were included in dextran 2,000,000. Endothelial cells suspended in same medium were inoculated onto 35 mm Petri dishes treated with MacroPrep granules and dextran 2,000,000.

Figure 3:
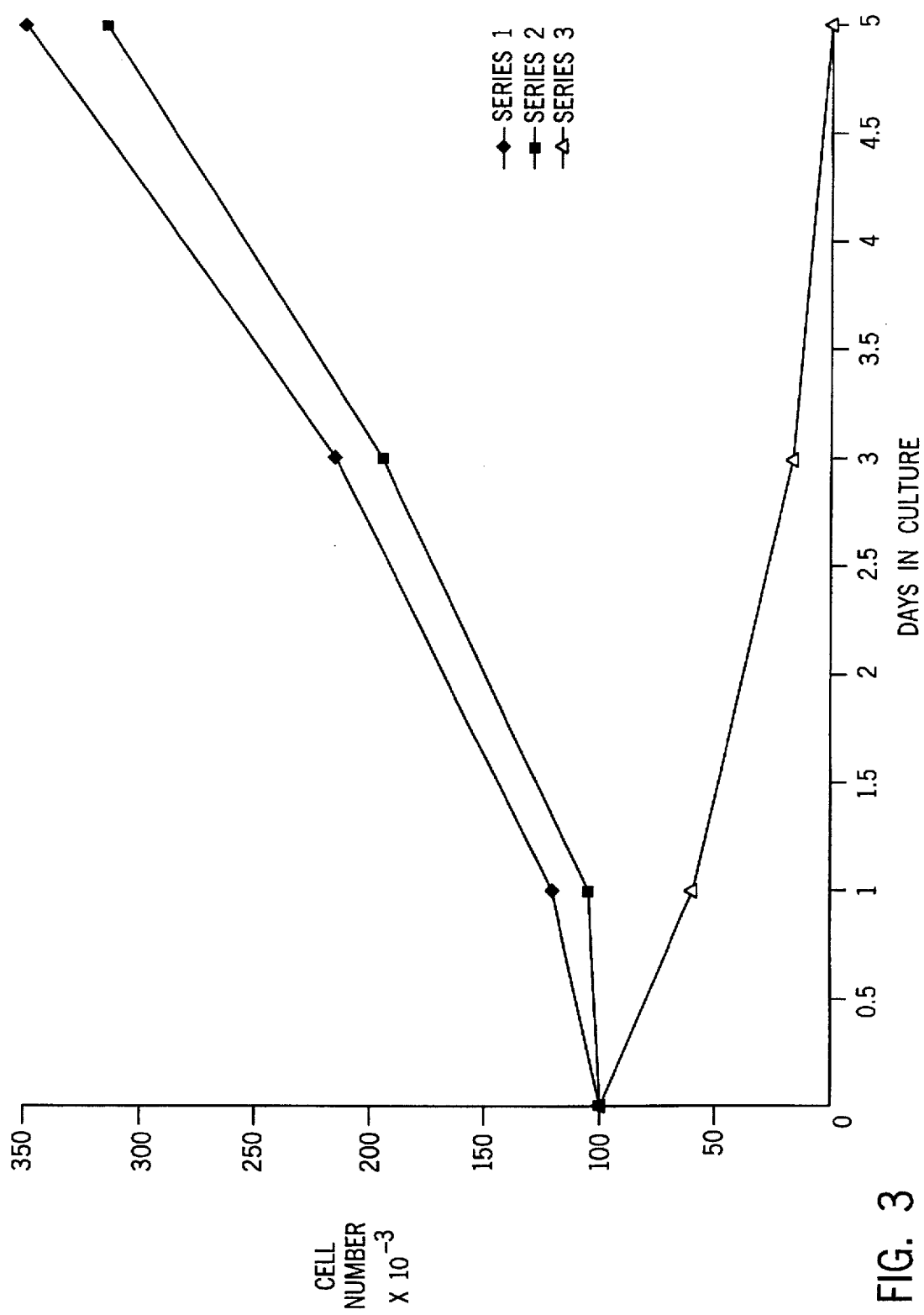
FIG. 3 is a graph illustrating the ability of the reinforced biological sealant of the present invention to potentiate endothelial cell growth.

Bovine endothelial cells, seeded at a density of 50,000 cell/ml, readily attached to the fibrin surface. Attachment efficiency was 72.5±1.32%. By contrast, the pure MacroPrep/dextran surface provided, not unexpectedly, little support for cell attachment (34.8±4.5%). FIG. 3 demonstrates the capacity of the RBS composition to potentiate endothelial cell growth. The cell growth on the control surface stopped after 3 days in culture, cell number decreased at 5 days (series 3). On the other hand, cell number increased on the RBS-type compositions, and reached density nearing confluence at 5 days (series 1 and 2).

Example 5

Insulin exerts profound effects on nutrient metabolism and induces the healing process. Therefore, intact insulin (1.0 g/liter-20 g/liter, preferred 5.0 g/liter) was included in an RBS of the present invention, for later release of the hormone into wounds or ulcers. Purified porcine insulin was obtained from Eli Lilly Co. (Indianapolis). Thrombin was purchased from Johnson & Johnson Medical Inc. (Arlington, Tex.). The following composition was used:

TABLE 15

| Component | Amount |
| --- | --- |
| Fibrinogen | 10 g/liter |
| Sodium Chlorate | 5.0 g/liter |
| Aprotinin | 0.5 g/liter |
| Insulin | 5.0 g/liter |
| Ficoll 400 | 200 g/liter |

We observed that the insulin included in composition was stable when it contracted with the purulent contents of wound and was released at constant rate (Table 16):

TABLE 16

| Time, hrs | Insulin concentration, picomole |
| --- | --- |
| 1 | 13 |
| 12 | 15 |
| 24 | 18 |
| 48 | 14 |
| 72 | 19 |
| 96 | 12 |

The reinforced biological sealants of the present invention are useful in all cardiovascular procedures where the patient is heparinized because such sealants do not require the patient's hemostatic system to be intact. Because the biological sealants of the present invention can be custom shaped, such biological sealants can be used in a wide variety of applications. Many of these applications were difficult to accomplish with the liquid applied fibrin glues of the prior art.

Such uses include aesthetic and plastic surgery (skin grafts placement, reapplication of cutaneous and subcutaneous tissues, healing of diabetic ulcers, bone grafts placement, tram flap, radical neck, face lift, decubitus ulcer); Otolaryngologic surgery (rhinoplasty myringoplasties, ossicular chain reconstruction, obliteration of attic and mastold spaces); general surgery (preventing exsanguinating hemorrhage, improving wound healing, hip and knee replacement, spine, Achilles tendon rupture, tracheal surgery, sealing of recurrent, spontaneous pneumothorax and closure bronchopleural fistulas, rupture and transplantation, repair of myocardial injuries, tetralogy of Fallot, repair of splenic lesions, rupture and transplantation, sealing partial kidney resection or ruptures, sealing vessel prostheses and stitches, graft surfaces, pancreatic duct plasty, repair of liver injuries); gynecology and microsurgery (fallopian tube anastomosis, tuboplasty); neurosurgery (dural leaks, craniofacial bone and soft tissue, microneural repairs, repair cerebral and dural defects, sealing subarachoid space); oncology (sealing of tumor surfaces after resection, topical chemotherapy, preventing seroma formation); and urology (heminephrectomy, vaso vasostomy, radical prostatectomy).

We claim:

1. A reinforced, prefabricated biological sealant, the sealant comprising:

a) a fibrinogen composition adapted to be applied to a treatment condition, and b) a thrombin composition layered on the fibrinogen composition, wherein at least one of the fibrinogen or thrombin composition comprises a reinforcement filler so that the sealant comprises a reinforcement filler, wherein the sealant has a critical pressure of at least 150 mm Hg at two minutes, and wherein the sealant is a solid film.

2. The sealant of claim 1 wherein the fibrinogen composition is a solid.

3. The sealant of claim 2 wherein the fibrinogen composition is a film.

4. The sealant of claim 1 wherein the thrombin composition is a solid.

5. The sealant of claim 4 wherein the thrombin composition is a film.

6. The sealant of claim 1 wherein the thrombin composition is a solution.

7. The sealant of claim 1 wherein the thrombin composition comprises a reinforcement filler.

8. The sealant of claim 1 wherein the fibrinogen composition comprises a reinforcement filler.

9. The sealant of claim 1 wherein the filler is selected from the group consisting of polyethylene glycol, myo-inositol, polyvinylpyrrolidone, bovine serum albumin, dextran, mannitol, sodium chlorate, and FICOLL.

10. The sealant of claim 1 wherein a colored indicator substance is added to at least one of the compositions.

11. The sealant of claim 10 wherein the colored substance indicates the formation of the mesh by a color change.

12. The sealant of claim 1, wherein the sealant has a critical pressure of at least 200 mm Hg at two minutes.

13. The sealant of claim 1 wherein the sealant has a critical pressure of at least 320 mm Hg at two minutes.

14. A reinforced, prefabricated biological sealant, the sealant comprising:

a) a fibrinogen composition adapted to be applied to a treatment condition, and b) a thrombin composition layered on the fibrinogen composition, wherein at least one of the fibrinogen or thrombin composition comprises a reinforcement filler so that the sealant comprises a reinforcement filler, wherein the sealant has a critical pressure of at least 150 mm Hg at two minutes, wherein the sealant is a solid film, and wherein the fibrinogen and thrombin compositions are dried for 5 to 24 hours at temperatures in the range of 10° C. to 50° C., at a pressure in the range of 25 Torr to 300 Torr.

15. The sealant of claim 14, wherein the sealant is dried at about 15° C. for about 6 hours at about 50 Torr.

* * * * *